United States Patent
Piraka (10) Patent No.: US 6,315,183 B1
(45) Date of Patent: Nov. 13, 2001

(54) DISPOSABLE SURGICAL STAPLER CARTRIDGE

(76) Inventor: Hadi A. Piraka, 21257 Woodfarm, Northville, MI (US) 48167

( * ) Notice: Subject to any disclaimer, the term of this patent is extended or adjusted under 35 U.S.C. 154(b) by 47 days.

(21) Appl. No.: 09/613,363

(22) Filed: Jul. 10, 2000

Related U.S. Application Data (62) Division of application No. 09/145,443, filed on Sep. 2, 1998, now Pat. No. 6,131,790.

(51) Int. Cl.⁷ .................................................. A61B 17/068
(52) U.S. Cl. ..................... 227/176.1; 227/19; 227/180.1
(58) Field of Search ................................ 227/19, 176, 1, 227/179.1, 180.1, 120, 156, 139, 124; 606/219, 139; 206/339, 340

(56) References Cited

U.S. PATENT DOCUMENTS

| | | | |
|---|---|---|---|
| 3,269,630 | * | 8/1966 | Fleischer ................................ 227/19 |
| 3,315,863 | * | 4/1967 | O'Dea ................................... 227/19 |
| 3,490,675 | * | 1/1970 | Green et al. ............................ 227/19 |
| 4,589,582 | * | 5/1986 | Bilotti ................................... 227/19 |
| 4,607,638 | * | 8/1986 | Crainich ................................ 606/219 |
| 4,608,981 | * | 9/1986 | Rothfuss et al. ........................ 227/19 |
| 4,805,823 | * | 2/1989 | Rothfuss ................................ 227/19 |
| 4,819,853 | * | 4/1989 | Green .................................... 227/19 |
| 4,821,939 | * | 4/1989 | Green .................................... 227/19 |
| 4,903,697 | * | 2/1990 | Resnick et al. ......................... 227/19 |
| 5,221,036 | | 6/1993 | Takase . | |
| 5,342,396 | * | 8/1994 | Cook ..................................... 227/19 |
| 5,551,622 | * | 9/1996 | Yoon ..................................... 227/19 |
| 5,560,532 | | 10/1996 | DeFonzo et al. . | |
| 5,919,198 | * | 7/1999 | Graves et al. .......................... 227/176.1 |

* cited by examiner

*Primary Examiner*—Scott A. Smith
(74) *Attorney, Agent, or Firm*—Alex Rhodes

(57) ABSTRACT

A disposable surgical stapler cartridge having a pair of partially engaged staple retaining and unloading members and a plurality of staples for joining together body tissues. Each staple has a center portion and a pair of adjoining downward extending side portions. Lower portions of the side portions are modified in cross-section to provide hinge points which reduce the required force for clinching the staples. The apertures of the cartridge retaining member require higher initial forces for unloading the staples from the member. The cartridge is detachably mounted in a jaw of a stapler by a pair of rails which slidably engage channels of the jaw and a boss which forcibly engages an aperture of the jaw. During a clinching of the staples the cartridge members are fully engaged to reduce the size of the cartridge.

8 Claims, 6 Drawing Sheets

DISPOSABLE SURGICAL STAPLER CARTRIDGE

RELATED U.S. APPLICATION DATA

Division of application Ser. No. 09/145,443 filed on Sep. 2, 1998, now U.S. Pat. No. 6,131,790.

FIELD OF THE INVENTION

This invention relates to surgical instruments and, more particularly, to an improved stapler and cartridge for joining layers of body tissues.

BACKGROUND OF THE INVENTION

Since the introduction of surgical staplers, they have enjoyed substantial success with surgeons for a variety of procedures. Staplers have improved many surgical procedures because of their ability to perform uniform tissue-fastening and consistent results with a squeeze of a handle. In meeting the ever-increasing demand for improvements, numerous changes have been made over the years in surgical staplers and cartridges. However, in spite of the substantial success which staplers have enjoyed and the substantial efforts expended in achieving improvements, several areas have remained completely incapable of resolution, until the present invention.

U.S. Pat. No. 4,354,628; U.S. 4,566,620; U.S. 5,111,987; and U.S. 5,425,745 are exemplary of currently used staplers which exist in the prior art. One characteristic feature of these staplers is that pusher bars and complex linkages are used to clamp, connect and divide layers of body tissues. Another characteristic feature is that they are disposable.

One of the principal drawbacks encountered with current staplers is their high costs. Despite their advantages over needles and thread, staplers have been under-utilized because of their high costs. Much of the high costs is due to complexity and numerous internal parts which are difficult to clean and sterilize. These difficulties have resulted in a practice of disposing staplers after a single use. Costs of disposing staplers has been somewhat offset by the use of plastic materials, however, a substantial cost penalty continues to exist.

Another drawback with some current staplers is that actuation of separate levers are required to clamp body tissues and to clinch staples.

Another drawback with some current staplers and cartridges is their size which limits their applications.

SUMMARY OF THE INVENTION

All of the drawbacks and difficulties encountered with current staplers are completely overcome with the present invention. In order to overcome these drawbacks, the present invention provides a reusable stapler which is easily cleaned and sterilized, is adaptable to endoscopic and open wound surgery and is improved in function.

In a first aspect of the invention, a pair of jaws are pivotally connected along a common centerline with a pivot axis of a pair of interconnected handles to join layers of body tissue with closely spaced rows of wire staples. The staples are supplied in a disposable cartridge which is detachably mounted in one of the jaws. The cartridge may also include a knife for separating the body tissues between a pair of adjacent rows of staples.

One advantage of the first aspect is that the jaws and handles are exposed for cleaning and sterilizing with existing methods and equipment. Another advantage is that a high force with minimum friction is provided for firing and clinching staples. The high force and minimum friction improves a surgeon's control over operation of the stapler. Another advantage is that the handles are used for clamping body tissues and clinching staples. Still yet another advantage is that complexity is substantially reduced over current staplers. Another feature of the invention is that a detent is provided on the handles' pivot axis for clamping and positioning the stapler prior to clinching the staples. The detent permits a surgeon to clamp and inspect the position of the stapler with respect to body tissues before clinching staples. If the surgeon is satisfied with the position of the staples, a simple squeeze of a handle fires the staples through the tissue and clinches the ends of the staples.

The cartridge which itself is believed to be novel consists of a staple retaining member and a staple ejecting member. The two members are initially partially engaged to ensure proper alignment of the staples with a staple ejecting member. One advantage of the cartridge, as will be fully understood in an ensuing detailed description, is that the size of the cartridge is reduced during the clinching of the staples. This assists a surgeon in removing the stapler more easily from surgical fields, including endoscopic surgery. An optional feature of the cartridge is that pre-formed hinge points are provided to reduce the required force for clinching the staples. This permits the stapler to be reduced.

In a second aspect of the invention, a pair of pivotally connected members serve as handles and jaws for clamping layers of body tissue and clinching parallel arranged rows of staples. The staples are provided in a disposable cartridge heretofore described.

In a third aspect of the invention, a pair of handles are connected to a pair of pivotally connected jaws by a pair of short links and a long slender rod.

In employing the teaching of the present invention, a plurality of additional alternate constructions can be developed to achieve the desired features of the current invention. The embodiments herein described are intended as examples and should not be considered as limiting the scope of the present invention.

Further benefits and features of the invention will become apparent from the ensuing detailed description and drawings which disclose the invention. The property in which exclusive rights are claimed is set forth in each of the numbered claims at the conclusion of the detailed description.

BRIEF DESCRIPTION OF THE DRAWINGS

The invention will be better understood and further objects, characterizing features, details and advantages thereof will appear more clearly with reference to the diagrammatic drawings illustrating specific embodiments of the invention by way of non-limiting example only.

DETAILED DESCRIPTION OF THE PREFERRED EMBODIMENT

Referring now to the drawings wherein like numerals designate like and corresponding parts throughout the several views, a first embodiment 30 of a surgical stapler 31 and cartridge 36, according to the invention is illustrated in FIGS. 1 through 16, inclusive. Since numerous alterations or modifications can be made in the first embodiment and other embodiments detailed herein, without departing from the scope of this invention, the following detailed disclosure, and the remaining embodiments shown and discussed, are intended as examples for achieving the present invention and are not intended, in any way, to limit the scope of the present invention.

In the orientations of the drawings, the stapler 31 is comprised of an upper handle 33 pivotally connected to a lower handle 32. each having an end point 33A, 32A pivotally connected to an end point of a pair of pivotally connected jaws 34, 35. A disposable cartridge 36 is detachably mounted in the upper jaw 34. The lower jaw 35 serves as an anvil and cooperates with the upper jaw 34 and cartridge 36 to clamp layers of body tissue 38 and connect the tissue with rows of staples 39.

Figure 1:
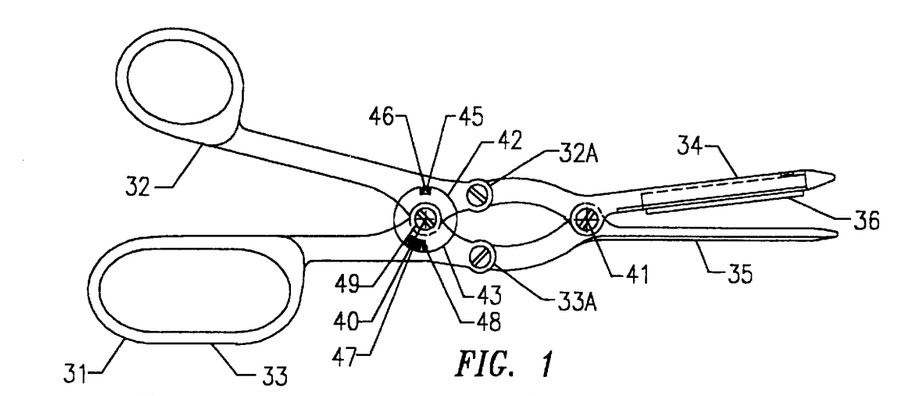
FIG. 1 is a front view of a first embodiment of a stapler and cartridge having a pair of jaws in open relationship according to the present invention.
Figures 2, 3:
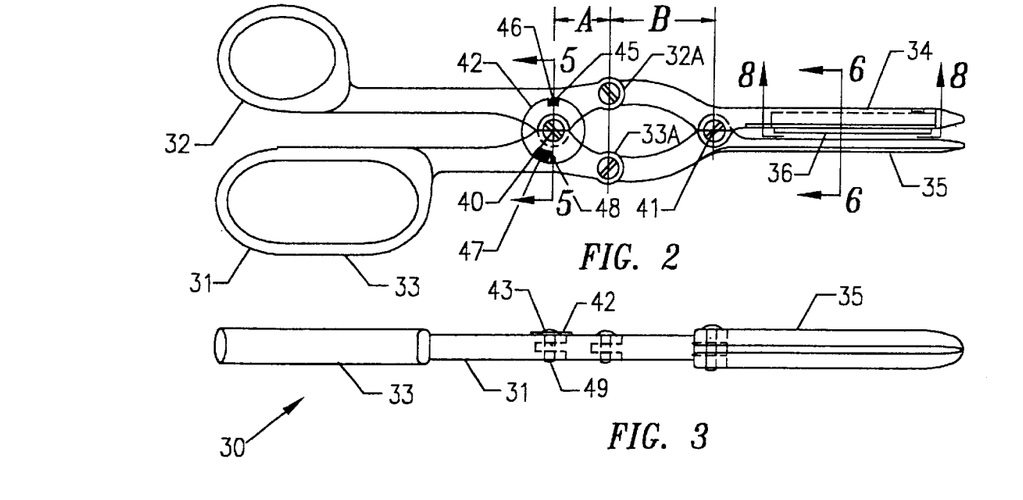
FIG. 2 is a front view of the stapler and cartridge with the pair of jaws in closed relationship.
FIG. 3 is a bottom view of FIG. 2.
Figure 4:
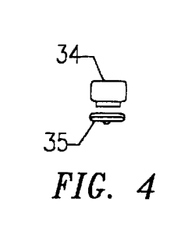
FIG. 4 is an end view of FIG. 2.

With reference to FIGS. 1 and 2, it will be observed that the pivot axis 40 of the handles 32, 33 and the pivot axis 41 of the jaws 34, 35 lie between the end points of the handles 32, 33 and jaws 34, 35. It will be further observed that when the handles 32, 33 are brought together the jaws 34, 35 close and that when the handles 32, 33 are separated the jaws 34, 35 open.

The stapler 31 has several important advantages over existing staplers. One advantage is reduced cost resulting from reduced complexity. Another advantage is that it can be easily cleaned and sterilized with existing methods and equipment. The difficulty in cleaning and sterilizing is about the same as cleaning and sterilizing surgical forceps in autoclaves of surgical facilities.

Another advantage is that when the handles 32, 33 are squeezed together a high force is produced for firing the staples 39 through the layers of body tissue 38 and clinching the end portions of the staples 39. This permits the stapler 31 to be offered in small sizes for procedures such as endoscopic surgery as well as in large sizes for procedures such as open surgery. Referring to FIG. 2, the magnitude of the force can be adjusted by varying the ratio of the distances "A" and "B" between the pivot axes 40, 41 of the handles 32, 33 and jaws 34, 35 and their inner end portions.

Figure 5:
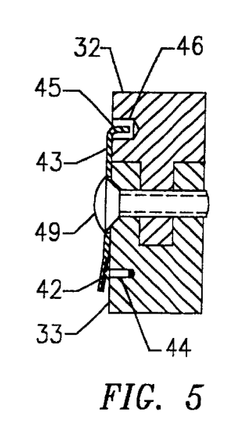
FIG. 5 is an enlarged cross-sectional view taken on the line 5—5 in FIG. 2 showing a resilient means for regulating the relative positions of the stapler's handles.

With reference to FIGS. 2 and 5, a detent 42 on the pivot axis 40 of the handles 32, 33 selectively regulates the relative positions of the handles 32, 33. The detent 42 allows the handles 32, 33 to be easily moved in increments together and apart during the clamping of the tissues 38 without firing the staples 39. The detent 42 is comprised of a thin resilient disk 43 which is centered on the pivot axis 40 of the handles 32, 33 and a post 44 which is fixed to the lower handle 33. The resilient disk 43 is keyed to the upper handle by engaging a tab 45 in an aperture 46 and rotates with the upper handle 33. During the rotation of the handles 32, 33, a plurality of radial depressions 47 of the disk 43 come into contact with a spherical head 48 of the post 44. The spacing and depth of the radial depressions can optionally be varied to require a higher force to fire the staples than the force to clamp the tissues. The teeth are formed in the disk by coining cutting or another suitable means. The resilient disk 43 is retained in the stapler 31 by the bolt 49 which pivotally connects the handles 32, 33.

The preferred construction of the cartridge 36 is best understood by reference to FIGS. 6 through 10 and 11 through 16, inclusive. In the orientation of the drawings, the cartridge consists of an upper generally rectangular shaped staple unloading member 50 and a generally rectangular shaped staple retaining member 51. The staple unloading member 50 has a thin upper wall 52, an adjoining thin outer wall 53 and rows of pusher blades 54 inside of the outer wall 53 which extend downwardly from the upper wall 52.

When the handles 32, 33 are squeezed together, the blades 54 push against the staples 39 to eject and fire the staples 39 through the layers of tissue 38 and clinch end portions of the staples 39. Extending along the sides of the unloading member's outer wall 53 are narrow rails 55. The rails 55 engage channels 56 of the stapler upper jaw 34 to support the cartridge 36 in the upper jaw 34. With reference to FIGS. 2 and 3, on the upper wall 52 of the unloading member 50 is a spherical boss 57. The height of the boss 57 permits the boss 57 to forcibly engage or disengage an aperture 58 of the upper jaw 34 when the rails 55 are engaged or disengaged with channels 56. The rails 55 and spherical boss 57 retain the cartridge 36 in the upper jaw 34. Mounted in the center of the unloading member 50 is a sharp knife 59 for separating the tissues 38 between inner rows of staples 39 during the clinching of the staples 39.

Figure 6:
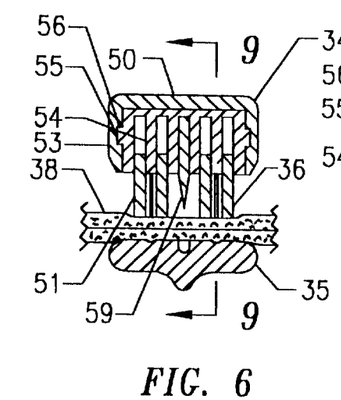
FIG. 6 is an enlarged cross-sectional view taken on the line 6—6 in FIG. 2 showing the condition of the cartridge during a clamping of two layers of body tissue prior to a clinching of the staples.
Figure 7:
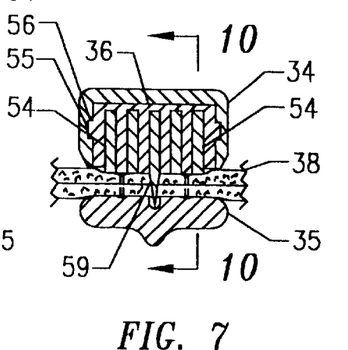
FIG. 7 is an enlarged cross-sectional view taken in a similar manner to FIG. 6 showing the condition of the cartridge after the staples have fired through the two layers of body tissue and clinched.
Figure 8:
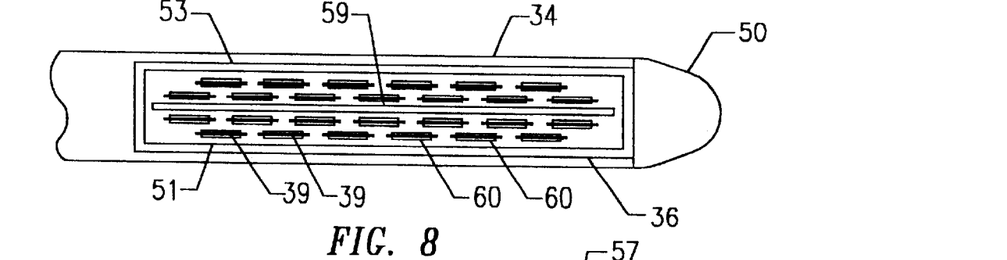
FIG. 8 is an enlarged cross-sectional view taken on the line 8—8 in FIG. 2 showing the manner of locating the staples and knife in the cartridge.

With reference to FIGS. 6 through 8, the staple retaining member 51 is pre-assembled to the staple unloading member 50 by partially engaging the lower portion of the unloading member 50 with an upper portion of the retaining member 51. During a firing and clinching of the staples 39, the overall size of the cartridge 36 is reduced as the staple unloading member 50 fully engages the staple retaining member 51. The reduction in cartridge size facilitates a withdrawal of the cartridge 36 during surgery.

Figure 15:
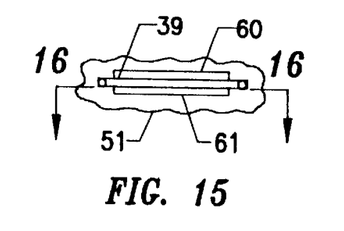
FIG. 15 is an enlarged partial view of FIG. 11 showing one of the staples.
Figure 16:
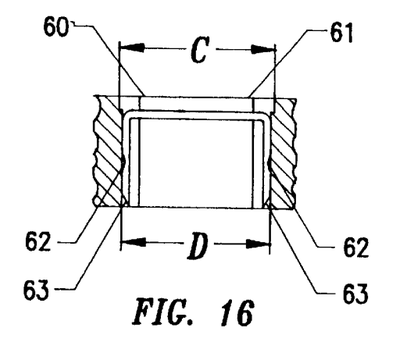
FIG. 16 is an enlarged cross-sectional view taken on the line 16—16 in FIG. 15.

Referring to FIG. 15, prior to firing, the staples 39 are individually stored in the retaining member 51 in slotted openings 60. The center portions 61 of the slotted openings 60 are preferably enlarged to reduce friction and the difficulty in manufacturing the cartridge 36. With reference to FIG. 16, the upper portions "C" of the slotted openings 60 wherein the staple ejecting member 51 is pre-assembled, are preferably slightly enlarged over the lower portions "D" of the slotted openings 60 which engage the end portions of the staples 39, to require a higher force to fire the staples 39 than the force for pre-assembling the members 50, 51. A higher force is desirable to deter surgeons from firing the staples 39 before the cartridge 36 is properly positioned.

Figure 11:
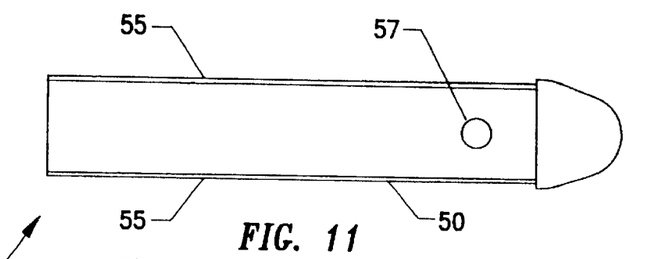
FIG. 11 is an enlarged bottom view of the cartridge.
Figures 12, 14:
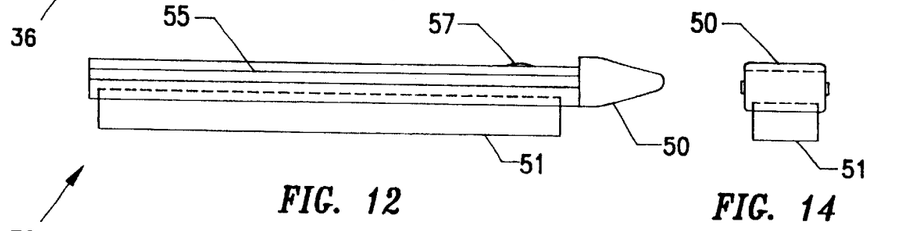
FIG. 12 is an enlarged left side view of the cartridge.
FIG. 14 is an enlarged end view of the cartridge.
Figure 13:
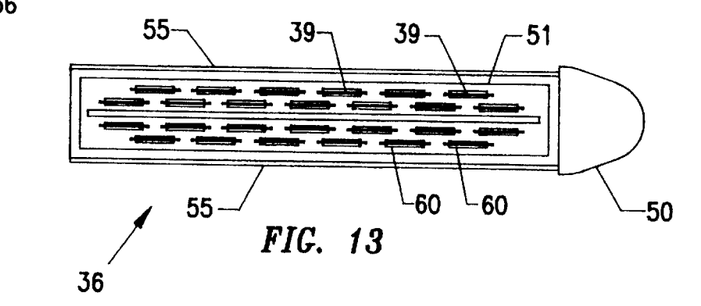
FIG. 13 is an enlarged plan view of the cartridge.

The designs of the staples 39 and their slotted openings 60 is shown in FIGS. 15 and 16. Several features reduce the force requirements for firing and clinching the staples 39. Lower forces allow the stapler and cartridge to be reduced in size. One optional feature consists of pre-forming hinge points 62 at the lower end portions of the staples 39. Another feature consists of sharp end portions of the staples. Staples 36 of adjacent rows are preferably staggered as shown in FIG. 11. Although four rows of staples 39 and a knife 59 shown, it will be apparent that fewer or greater numbers of rows can be provided, with or without the knife.

Figures 17, 19, 20, 21, 22:
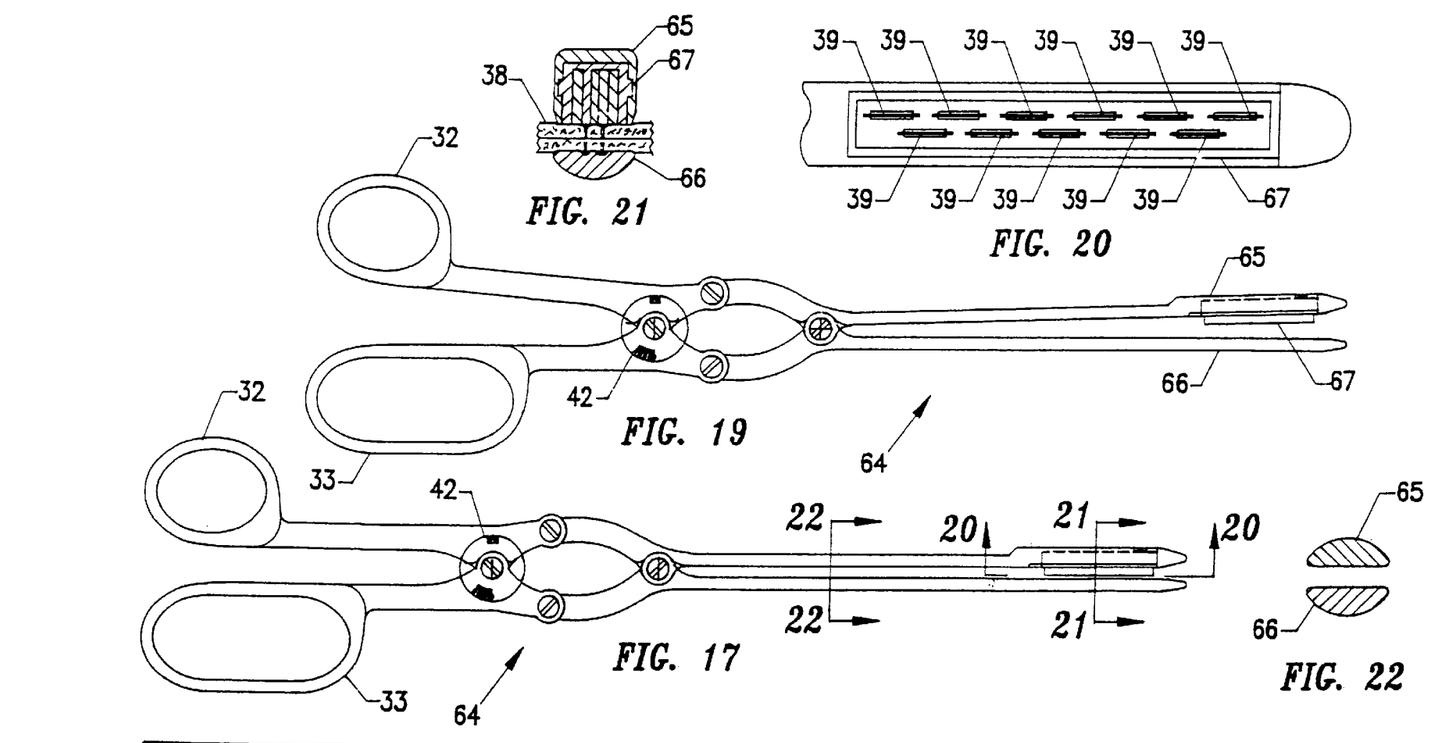
FIG. 17 is a front view of an alternate embodiment having elongated jaws.
FIG. 19 is a front view of the alternate embodiment showing the jaws in an open condition.
FIG. 20 is an enlarged cross-sectional view taken on the line 20—20 in FIG. 17.
FIG. 21 is an enlarged cross-sectional view taken on the line 21—21 in FIG. 17 showing the condition of the cartridge after the staples have fired through two layers of body tissue and clinched.
FIG. 22 is an enlarged cross-sectional view taken on the line 22—22 in FIG. 17.
Figure 18:
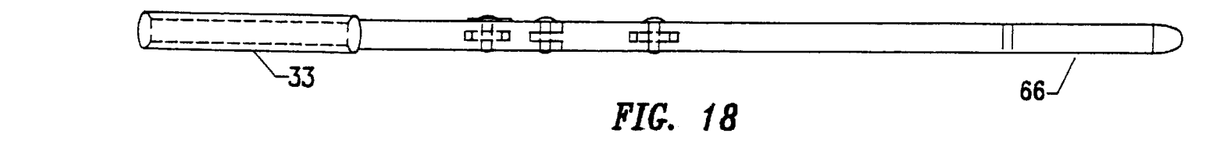
FIG. 18 is a bottom view of the alternate embodiment.

Referring now to FIGS. 18 through 22, inclusive, an embodiment 64 is shown with elongated jaws 65, 66 and a reduced size cartridge 67 for endoscopic surgery. As shown in FIGS. 20 and 21 the cartridge 67 has been reduced in size by eliminating the knife 59 and providing only two or three rows of staples 39.

Figure 23:
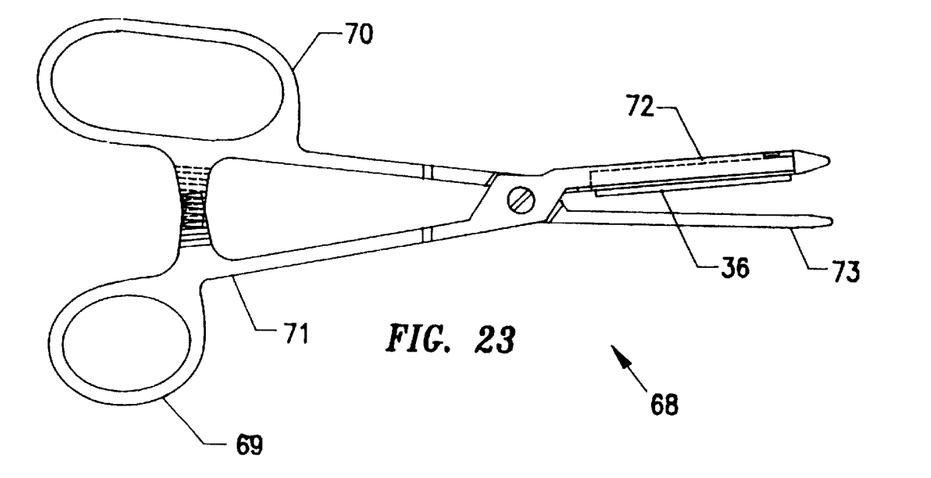
FIG. 23 is a front view of a third embodiment showing a pair of jaws in an open position.
Figure 24:
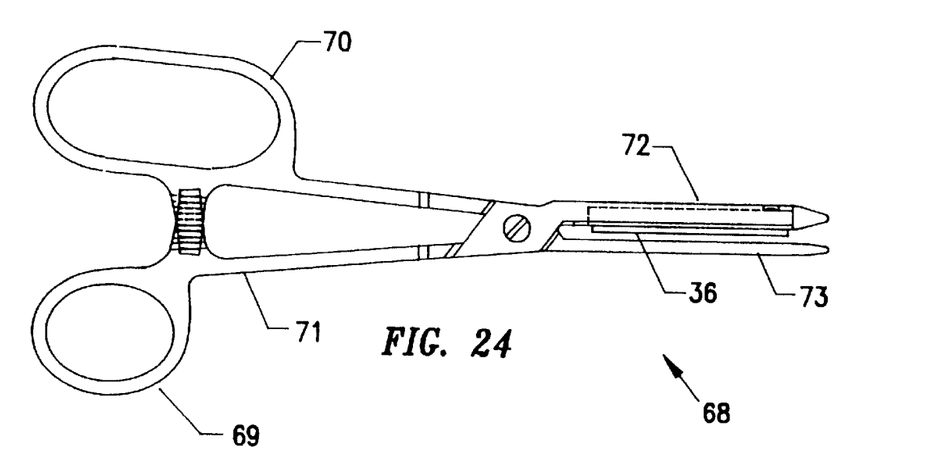
FIG. 24 is a front view of the second embodiment showing the pair of jaws in a closed position.
Figure 25:
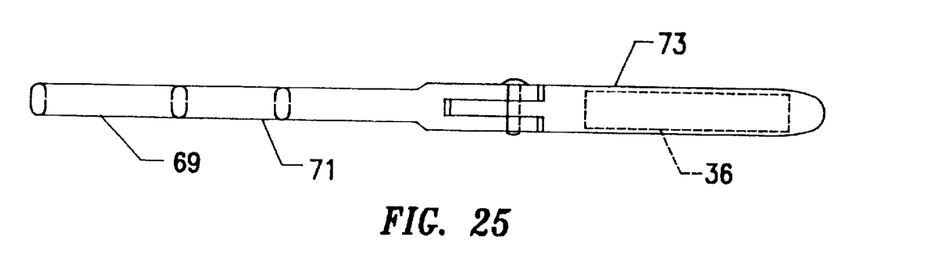
FIG. 25 is a bottom view of the second embodiment.

In FIGS. 23 through 25, an embodiment 68 is shown for open surgery. The stapler 69 resembles a pair of standard forceps wherein end portions of pivotally connected upper 70 and lower 71 handles form upper 72 and lower 73 jaws. It will be observed in this embodiment 60 that when the handles 70, 71 are brought together the jaws 72, 73 open and when the handles 70, 71 are separated the jaws 72, 73 close. As shown in FIG. 24, the cartridge 36 is preferably parallel to the lower jaw 73 at the point of firing and clinching the staples whereas in the usual forceps, the upper jaw is parallel to the lower jaw when the jaws are closed.

Figure 26:
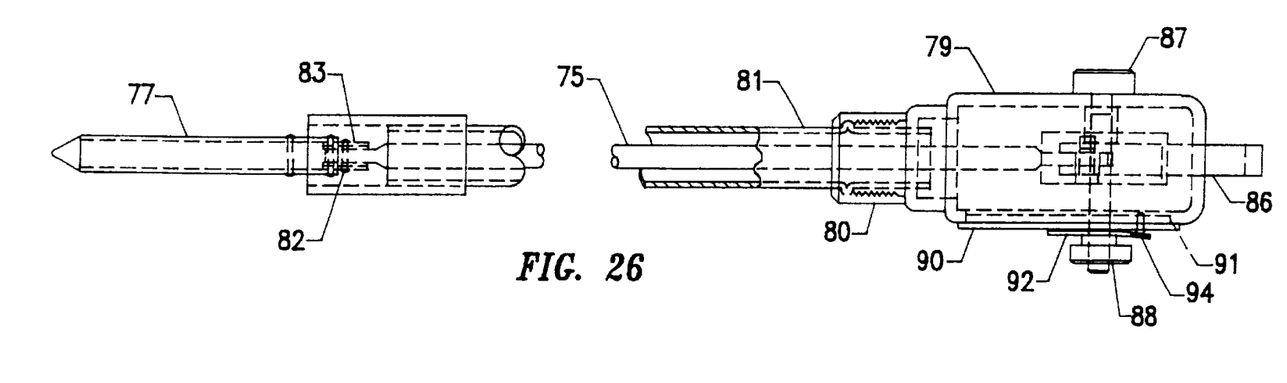
FIG. 26 is a fragmentary plan view of a fourth embodiment.
Figure 27:
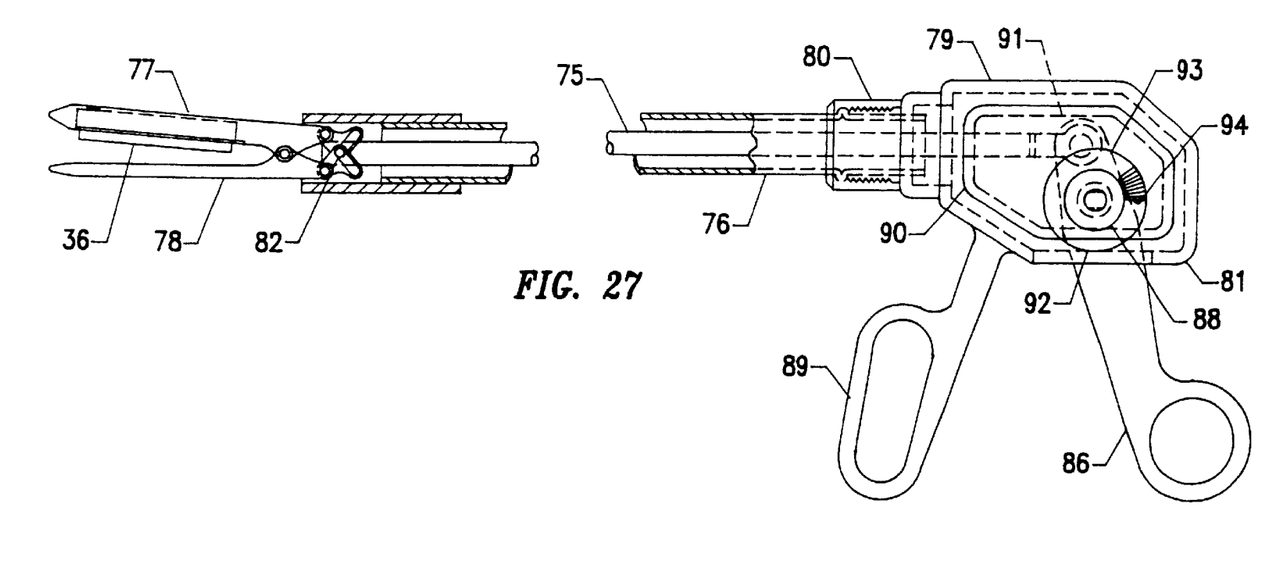
FIG. 27 is a fragmentary front view of the fourth embodiment.

In FIGS. 26 and 27 an embodiment 74 is shown for endoscopic surgery. A rod 75, housed in a tube 76, opens and closes a pair of jaws 77, 78. One end of the tube 76 is attached to a housing 79 with a threaded nut 80 to allow the tube 76 to be detached during a cleaning and sterilizing of the stapler 81.

One end of the rod 75 is connected by a pin 82 to a pair of slotted links 83. Opposite ends of the links 83 are pivotally connected to upper 77 and lower 78 jaws and open and close the jaws 77, 78 when the links 83 are moved by the rod 75. The opposite end of the rod 75 is pivotally connected to a movable handle 86 by a pivot bolt 87 and nut 88 which attach the handle 86 in the housing 79.

One portion of the housing 79 extends downwardly to form a fixed handle 89. A removable cover 90, attached by the bolt 87 and nut 88 spans an access opening 91 and allows the rod 75 to be removed from the stapler 81 for cleaning and sterilizing. Thus, the stapler 81 can be easily disassembled for cleaning and sterilizing.

A detent is provided for selectively positioning the movable handle. The detent 92, comprised of a thin resilient disk 93 which rotates with the handle 86 and post 94 which is fixed to the housing 79 selectively positions the handle 86.

Figure 9:
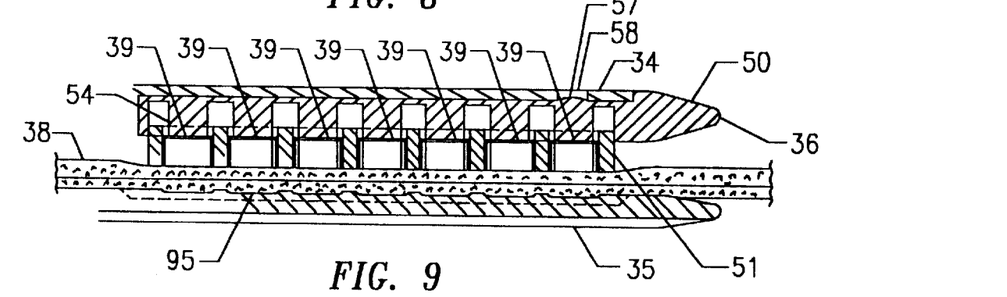
FIG. 9 is an enlarged cross-sectional view taken on the line 9—9 in FIG. 6.
Figure 10:
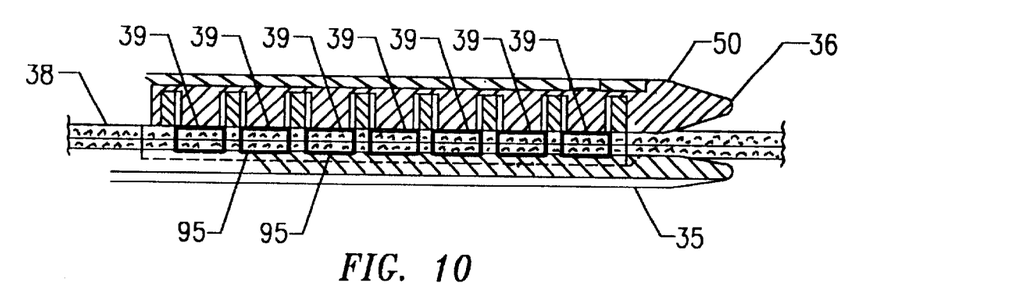
FIG. 10 is an enlarged cross-sectional view taken on the line 10—10 in FIG. 7.

Referring again to FIGS. 1 through 16, inclusive, in the typical use of the present invention, the cartridge 36 is installed by advancing the rails 55 in the channels 56 and forcibly engaging the spherical boss 57 with the aperture 58. The jaws 34, 35 are opened as shown in FIG. 1, and the layers of tissue 38 to be joined are positioned between the jaws 34, 35. The handles 32, 33 are squeezed by an amount which is sufficient to apply a light clamping pressure to the layers of tissues 38 as shown in FIGS. 6 and 9. During the clamping of the tissues 38, a clicking effect is produced by the detent 42 when the handles 32, 33 are moved apart as well as together. The clicking effect enables a surgeon to judge the travel of the handles 32, 33 before firing the staples 39. By counting the clicks during the opening and closing of the handles 32, 33, the surgeon can avoid a premature firing of the staples 39.

After the tissues 38 have been clamped, the position of the jaws 34, 35 relative to the tissues 38 is inspected. If the surgeon is not satisfied, the jaws 34, 35 are opened, repositioned, and closed. When the surgeon is satisfied that the stapler is properly positioned, the handles 32, 33 are tightly squeezed to fire and clinch the staples 39 in the manner shown in FIGS. 7 and 10.

During the clinching of the staples 39, their pointed end portions 63 contact depressions 95 in the lower jaw 35 which bias the pointed end portions 63 of the staples 39 inwardly. After the clinching of the staples 39 the jaws 34, 35 are opened, the stapler 31 is removed and the spent cartridge 36 is withdrawn from the stapler 31 and discarded.

In the foregoing detailed disclosure of the invention, the construction of the surgical stapler and cartridge and the method of using them have been fully detailed. In addition, alternate embodiments and constructions have been discussed as a part of this detailed disclosure.

It will be appreciated that other embodiments can be developed by changes in shape, material, arrangement of parts, and substitution of parts without departing from the spirit thereof.

Having described my invention, what I claim as new and desire to secure by Letters Patent is:

1. In a disposable cartridge having a plurality of staples for joining together opposite sides of an incision, the improvement comprising: said cartridge having a pair of generally rectangular shaped members with telescopically engaging outer portions, one of said members being a staple retaining member for storing said plurality of staples and the other of said members being a staple unloading member in partial engagement with said staple retaining member for unloading said staples from said staple retaining member; said staple retaining member having a plurality of slotted apertures for storing said staples, each of said apertures having a means for preventing a premature unloading of one of said staples from said staple retaining member during a positioning of said cartridge on said opposite sides of said incision, said means comprising said slotted apertures having upper portions which are slightly enlarged relative to lower portions to require a force for unloading said staples from said staple retaining member which is higher than a force which is required for assembling said staple retaining member to said staple unloading member.

2. The improvement as defined in claim 1 wherein said cartridge further comprises a sharp knife blade for separating said layers of body tissue adjacent to said row of staples.

3. The improvement as defined in claim 1 wherein said cartridge has at least two rows of staples in parallel relationship to each other.

4. The improvement as defined in claim 3 wherein said cartridge has an inner pair of rows of staples; an outer pair of rows of staples and a sharp knife between each row of said inner pair of rows of staples.

5. The combination as defined in claim 1 wherein one of said cartridge members has a pair of outer rails and the other of said cartridge members has a pair of outer channels for slidably engaging said rails and a projection on one of said members for forcibly engaging a jaw of a stapler to detachably mount said cartridge in said stapler.

6. In combination with a stapler having a pair of pivotally connected jaws, a disposable cartridge detachably mounted in said jaws, said cartridge comprising: a staple retaining member mounted in one of said jaws and having a plurality of slotted apertures for storing a plurality of staples, each of said slotted apertures having a means for preventing a premature unloading of said staples from said staple retaining member; said means comprising said slotted apertures having upper portions which are slightly enlarged relative to over lower portions to require a force for unloading said staples from said staple retaining member which is higher than a force which is required for assembling said staple retaining member to a staple unloading member; a staple unloading member for unloading said staples from said staple retaining member; said unloading member having a plurality of blade shaped portions in partial engagement with said plurality of slotted apertures of said staple retaining member; and a plurality of staples stored in said slotted apertures of said retaining member, each of said staples having a center portion and a pair of adjoining downward extending side portions.

7. The combination set forth in claim 6 wherein lower end portions of each of said downward extending side portions of each of said staples has a preformed hinge portion for reducing the force which is required to clinch said end portion of said staple.

8. The combination set forth in claim 6 wherein each of said slotted apertures has side portions in close fitting relationship said downward extending portions of one of said staples and a center portion in loose fitting relationship with said center portion of said staple.

\* \* \* \* \*